Figure 1:

United States Patent [19]

Laurer et al.

[11] 4,009,124
[45] Feb. 22, 1977

[54] BASIC MIXED CARBONATE OF COPPER AND ALUMINUM AND PROCESS FOR MANUFACTURING A COPPER-CONTAINING CATALYST

[75] Inventors: Peter Rudolf Laurer, Ludwigshafen; Wolfgang Schroeder, Bad Durkheim; Herwig Hoffmann, Frankenthal; Heinz Lingk, Bobenheim-Roxheim, all of Germany

[73] Assignee: BASF Aktiengesellschaft, Ludwigshafen (Rhine), Germany

[22] Filed: Sept. 15, 1975

[21] Appl. No.: 613,525

[52] U.S. Cl. .......................... 252/463; 260/635 Y; 423/600
[51] Int. Cl.² ...................... B01J 21/04; B01J 23/72
[58] Field of Search .......................... 252/443, 463; 260/635 Y; 423/600

[56] References Cited

UNITED STATES PATENTS

| | | | |
|---|---|---|---|
| 3,896,053 | 7/1975 | Broecker et al. | 252/466 J |
| 3,941,721 | 3/1976 | Broecker et al. | 252/466 J |

*Primary Examiner*—W. J. Shine
*Attorney, Agent, or Firm*—Johnston, Keil, Thompson & Shurtleff

[57] ABSTRACT

Basic carbonate which contains copper and aluminum and is suitable for the manufacture of copper-containing catalysts and which has the general formula $Cu_mAl_6(CO_3)_{0.5m}O_3(OH)_{m+12}$, where m may be an integer or non-integer between 2 and 6.

4 Claims, 3 Drawing Figures

BASIC MIXED CARBONATE OF COPPER AND ALUMINUM AND PROCESS FOR MANUFACTURING A COPPER-CONTAINING CATALYST

This invention relates to copper-containing materials suitable as catalyst precursors for the manufacture of butynediol-1,4.

It is known to produce basic carbonates of the general formula $$Me(II)_nMe(III)_2(OH)_{16} \cdot 4 H_2O,$$

where the metal Me(II) is a divalent ion-forming metal and Me(III) is a trivalent ion-forming metal. According to German Pat. No. 2,024,282, these compounds have the structure of natural manasseite. Examples of metal atoms which may be included in this crystal structure are as follows:

Nickel, cobalt, magnesium, manganese, zinc, copper as Me(II), and aluminum, iron and chromium as Me(III).

Compounds of these metals having the crystal structure of manasseite are recommended as catalysts or catalyst precursors. The catalysts obtained are described as particularly active.

However, their drawback is that they are frequently insufficiently stable to thermal and even chemical influences. For example, if a compound of the metal composition $Cu_4Mg_2Al_2$ is held at 350° C for 6 hours, the copper is then mainly present in oxide form, as may be demonstrated by X-ray analysis. Furthermore, the magnesium is no longer resistant to the attack of weakly acid media.

We have now found a basic carbonate which contains copper and aluminum and which is particularly suitable for the manufacture of copper-containing catalysts. It has the general composition $$Cu_mAl_6(CO_3)_{0.5m}O_3(OH)_{m+12},$$

where $m$ may be an integer or non-integer between 2 and 6, and has a number of advantages over carbonates of manasseite structure.

A basic carbonate of the composition of the invention may be obtained by mixing a preferably 1 M aqueous solution of salts of copper and aluminum which can be precipitated by carbonates, which solution contains copper and aluminum in an atomic ratio of copper to aluminum of $m:6$, with a preferably approximately 2 M solution containing an alkali metal carbonate and/or bicarbonate, such that the resulting mixture has a pH of from 8 to 9.5 and preferably from 8.1 to 8.5, the temperature of the mixture being maintained at from 60° to 90° C. The resulting precipitate may be washed and then be dried, if desired, at a temperature below 100° C. However, the invention is not restricted to the carbonates obtained by the above recipe. For example, other suitable solutions of aluminum and copper salts are those in which the total molar concentration is from about 0.05 to about 3. The amount and concentration of the alkali metal carbonate solution should contain an equivalent amount of carbonate and its molar concentration is preferably twice as great.

By determining the carbon dioxide, the water titratable according to Fischer and the total loss on ignition and by determining the copper and aluminum in appropriate samples in conventional manner, it has been possible to arrive at the aforementioned probable composition given in formula form.

The X-ray diagrams of the compounds (FIG. 1), in which the compound has the composition

Figure 2:

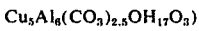

indicate a layer lattice. It has a remote similarity to the X-ray diagram of manasseite (FIG. 2), although it has characteristic properties which have not hitherto been described.

Table

| d-values of Guinier photographs (CuK$_\alpha$) | | | |
|---|---|---|---|
| New compound Cu$_5$Al$_6$ carbonate (FIG. 1) | | Cu$_3$Mg$_3$-Al$_2$ manasseite (FIG. 2) | |
| d | relative intensity | d | relative intensity |
| 7.65 | 100 | 7.65 | 100 |
| 3.80 | 90 | 3.80 | 80 |
| 2.72 | 50 | | |
| 2.52 | 70 | 2.58 | 80 |
| 2.41 | 40 | | |
| 2.39 | 10 | | |
| 2.24 | 50 | 2.28 | 60 |
| 2.03 | 20 | | |
| 1.89 | 50 | 1.94 | 40 |
| 1.72 | 30 | 1.73 | 10 |
| 1.59 | 10 | 1.63 | 10 |
| 1.56 | 30 | | |
| 1.54 | 10 | | |
| 1.52 | 30 | 1.53 | 30 |
| 1.47 | 30 | 1.50 | 30 |
| 1.44 | 30 | | |

*Remarks.* — The d-values may show slight deviations from those given above at various water contents. Slight impurities (Al(OH)$_3$) are usually found. Lines of low relative intensity were not measured, i.e. the above lists contain only the major lines.

It is seen that the compound of the invention is a novel compound of copper and aluminum. Presumably, the constant elements of the layer lattice in the novel material are formed by an aluminum oxide hydrate, whilst basic copper carbonate will be present in various amounts in the interstitial spaces. However, the layer lattice would seem to require, for its formation, that a certain minimum number of said interstitial spaces be filled.

When used industrially as catalyst, the novel compound has the particular advantage of being thermoresistant as regards the distribution of the copper. On heating to above 80° to 100° C, it liberates water and carbon dioxide and finally becomes amorphous, as determined by X-ray analysis. However, the fine distribution of copper and aluminum in the original compound seems to remain, surprisingly even when held for relatively long periods at temperatures at which the said distribution is lost in similar prior art compounds.

If a sample of the novel compound containing, for example, copper and aluminum in the ratio Cu$_5$Al$_6$ is held at 350° C for 6 hours, no lines of any kind are then found in the X-ray diagram. The sample remains amorphous even when tempered for 6 hours at 50° C, i.e. no recrystallization takes place, from which a uniform distribution of the copper in the heated sample may be concluded.

The range of existence of our novel compound is limited by two different factors, as already indicated. If the concentration of copper is too high, there is the increasing tendency of the copper no longer to precipitate as a mixed crystal in the form of the novel compound but as a pure copper compound in the form of malachite. It is not possible to manufacture the pure compound when the atomic ratio of copper to aluminum is as low as 11:10. In this case portions of both the novel compound and malachite are always found. At larger copper concentrations, the new compound is no longer found. From this it may be concluded that the number of interstitial spaces available for the copper is limited or that at a large excess of copper the mixture preferentially forms the malachite structure for thermodynamic reasons.

If the concentration of copper is too low, it will not be sufficient to form exclusively or stabilize the new lattice and there is always obtained the hydrargillite lattice. This is inevitably the case at atomic ratios of copper to aluminum of less than 2:6.

Compounds of the type claimed in the present invention may be prepared by precipitation from aqueous salt solutions with a basic carbonate-containing precipitant in aqueous solution. It is important to maintain a relatively narrow pH and temperature range. It has been found particularly suitable to use a basic pH range, particularly one from 8.0 to 8.5, and a temperature range of from 60° to 90° C and in particular one from 75° to 85° C. Suitable salts are, for example, nitrates, sulfates, acetates, formates and other water-soluble salts.

Suitable precipitants are alkali metal carbonates and bicarbonates, particularly sodium bicarbonate and mixtures of sodium carbonate and sodium bicarbonate having a pH of from 8 to 9.5. In some cases use may be made of, say, sodium hydroxide, if the copper and aluminum salts used show an acid reaction. A particularly suitable precipitant is a solution which has been obtained by heating water with (sparingly soluble) sodium bicarbonate in an amount of from 100 to 200 g/l, heating being continued until the bicarbonate is completely dissolved. As is well known, carbon dioxide is given off and a portion of the bicarbonate is converted to carbonate. Metal salt and precipitant are preferably used in approximately 1 M and 2 M solution respectively. Precipitation may be carried out continuously or batchwise.

The freshly precipitated substance may be amorphous, but it crystallizes on drying. Following elutriation of the mother liquor with cold water and drying of the precipitate at from 70° to 80° C, the latter always has the composition and structure claimed in the present invention.

To convert the above substance to a catalyst (e.g. a copper catalyst for the synthesis of butynediol from formaldehyde and acetylene or for carbon monoxide conversion), the compound is generally held ("annealed") for from 1 to 8 hours at 350° to 600° C and preferably from 500° to 550° C. Following milling and sifting to give a suitable particle size distribution, e.g. diameters of from 60 to 200 $\mu$, there is obtained a particularly active form which is preferably used for suspension catalysis. Alternatively, the annealed compound may be prepared in a discrete form suitable for use as a fixed-bed catalyst, e.g. ropes, pellets, spheres and rings.

The compounds of the invention are used industrially for the manufacture of catalysts. They are particularly suitable for ethynylation (e.g. the aforementioned preparation of butynediol), CO-conversion (particularly at low temperature) and methanol synthesis.

The manufacture of the compounds of the invention is described below in an Example. Compounds having a composition different from that given in the Example are prepared in a similar manner using various proportions of copper and aluminum salts. The use of the compounds is described in comparison with catalysts of the prior art.

EXAMPLE 1

Using commercially available nitrates of copper ($Cu(NO_3)_2 \cdot 3H_2O$) and aluminum ($Al(NO_3)_3 \cdot 9H_2O$) a mixed solution is prepared which contains one gram atom of Cu + Al per liter. The atomic ratio of copper to aluminum is set at 1:1.2 by using appropriately weighed amounts of the said salts. The precipitant solution is initially a 2 M solution of sodium bicarbonate. In order to dissolve the sparingly soluble sodium bicarbonate, the mixture is held at 80° C for one hour with occasional stirring. The precipitant is used in excess so that the molar ratio of sodium ions to nitrate ions is 1.55:1. The stirred container (capacity 10 liters) used for the precipitation is filled with water at 80° C in an amount sufficient for the stirrer blade to dip beneath the surface thereof. The two solutions are also held at 80° C. After starting the stirrer, the precipitant is first fed to the stirred container until the pH therein is 8.0. At this stage, the feed of nitrate solution at a rate of 5 l/hour is commenced. The feed rate of the precipitant solution is regulated so as to maintain a pH in the stirred container of from 8.0 to 8.5 throughout the precipitating period. Following precipitation, water is added so as to give a temperature of 70° C. Stirring is continued for one hour, after which the temperature has fallen to about 60° C. The major portion of the precipitated solid is washed with cold water a number of times until no more nitrate can be detected in the filtered washings by the Brucin method.

The precipitate is mechanically freed from washing water as far as possible and is then dried in a drying cabinet at from 70° to 80° C. After this treatment, the precipitate has an outwardly dry appearance and a turquoise-blue color and its X-ray diagram shows the lines typical of the novel compound. After annealing for 6 hours at 350° C, the color is olive green and after annealing for 6 hours at 550° C it is dark olive. Neither of the X-ray diagrams of these 2 annealed samples shows any lines.

Figure 3:

Comparison of compounds produced in the manner of the invention with catalysts of the prior art:

A compound having the same atomic concentration of Cu as in Example 1 was prepared in the manner described in Example 1 from the series of Cu-Mg-Al manasseites by known methods. The metals present in the compound had an atomic ratio of Cu:Mg:Al of 3.6:2.4:2.0. This compound having the typical X-ray diagram of manasseite (FIG. 2) was annealed for 4 hours at 350° C. The resulting substance had an X-ray diagram showing diffuse but distinct lines of CuO (FIG. 3).

EXAMPLES 2 TO 5

By varying the proportions, compounds may be obtained by the method described in Example 1 to give the following metal ratios:

The remaining components ($CO_3$, OH-radicals), O) correspond to the empirical formula of Example 1.

Application

The compound prepared in the manner described in Example 1 was annealed for 2 hours at 550° C. A sample of the resulting catalyst precursor was found to be amorphous when examined by X-rays and its color was dark olive. The particle size was between 60 and 200 $\mu$.

A sufficient quantity of this catalyst precursor was slurried in a 30% aqueous formaldehyde solution to give a suspension containing 3.8% w/w of catalyst precursor. The suspension was transferred to a heated reaction vessel and acetylene was introduced through the base of the vessel under atmospheric pressure, a neutral reaction being maintained by the addition of aqueous caustic soda solution.

The conversion of the divalent copper present in the catalyst precursor to the acetylide of monovalent copper begins above about 60° C and was carried to completion at 70° C.

After raising the temperature to 85° C, the degradation of the formaldehyde by reaction with the acetylene to form butynediol was followed analytically. It was found that after a reaction time of 3 hours 75% of the formaldehyde originally present had been converted to butyne diol.

We claim:

1. Basic mixed carbonate of copper and aluminum of the formula $$Cu_mAl_6(CO_3)_{0.5m}O_3(OH)_{m+12}$$

where $m$ is a number between 2 and 6.

2. A catalyst for the manufacture of butynediol, said catalyst being formed by precipitating, at pH 8 to 9.5 and a temperature of from 60° to 90° C,
   a. an aqueous dilute solution of copper and aluminum salts capable of being precipitated by carbonate, the copper and aluminum being present in said solution in an atomic ratio of m:6, $m$ being a number between 2 and 6, with
   b. an aqueous alkali metal carbonate or bicarbonate solution, the atomic concentration of alkali being about twice the concentration of copper and aluminum in said solution, whereby a composition is obtained of the formula $Cu_mAl_6(CO_3)_{0.5m}O_3$—$(OH)_{m+12}$, having the above definition, and thereafter drying and annealing the precipitate at 350° to 600° C.

3. A catalyst as set forth in claim 2 wherein said precipitate is annealed for from 1 to 8 hours.

4. A catalyst as set forth in claim 2, as obtained by annealing a composition having an X-ray diagram defined by d-values of Guinier photographs (CuK ), said d-values being substantially as follows: 7.65/100; 3.80/90; 2.72/50; 2.52/70; 2.41/40; 2.39/10; 2.24/50; 2.03/20; 1.89/50; 1.72/30; 1.59/10; 1.56/30; 1.54/10; 1.52/30; 1.47/30; 1.44/30; the figures representing the d-value and its relative intensity respectively.

* * * * *